(12) United States Patent
Van Duren

(10) Patent No.: US 8,454,672 B2
(45) Date of Patent: Jun. 4, 2013

(54) WARMING DEVICE FOR PERIOPERATIVE USE

(75) Inventor: Albert P. Van Duren, Chaska, MN (US)

(73) Assignee: Arizant Healthcare Inc., Eden Prairie, MN (US)

(*) Notice: Subject to any disclaimer, the term of this patent is extended or adjusted under 35 U.S.C. 154(b) by 240 days.

(21) Appl. No.: 11/057,403

(22) Filed: Feb. 11, 2005

(65) Prior Publication Data

US 2006/0184217 A1   Aug. 17, 2006

(51) Int. Cl.
*A61F 7/02* (2006.01)

(52) U.S. Cl.
USPC .......................................................... 607/108

(58) Field of Classification Search
USPC .................... 607/104, 108–112, 114
See application file for complete search history.

(56) References Cited

U.S. PATENT DOCUMENTS

| | | | | |
|---|---|---|---|---|
| 2,512,559 A | | 6/1950 | Williams | 5/347 |
| 2,540,547 A | * | 2/1951 | Rodert | 165/47 |
| 2,573,414 A | | 10/1951 | Dunn | 128/144 |
| 2,826,758 A | | 3/1958 | Kahn | 2/81 |
| 3,468,299 A | * | 9/1969 | Amato | 126/204 |
| 3,610,323 A | | 10/1971 | Troyer | 165/46 |
| 3,757,366 A | | 9/1973 | Sacher | 5/347 |
| 3,855,635 A | | 12/1974 | Ramirez | 2/114 |
| 3,911,499 A | | 10/1975 | Benevento et al. | 2/114 |
| 3,950,789 A | | 4/1976 | Konz et al. | 2/93 |
| 4,055,173 A | | 10/1977 | Knab | 128/139 |
| 4,146,933 A | | 4/1979 | Jenkins et al. | 2/2 |
| 4,194,247 A | * | 3/1980 | Melander | 2/457 |
| 4,369,528 A | | 1/1983 | Vest et al. | 2/69 |
| 4,494,248 A | | 1/1985 | Holder | 2/69 |
| 4,524,463 A | | 6/1985 | Ogden | 2/105 |
| 4,558,468 A | | 12/1985 | Landry et al. | 2/51 |
| 4,578,825 A | | 4/1986 | Vote | 2/114 |
| 4,587,671 A | | 5/1986 | Rodriguez, Jr. et al. | 2/69 |
| 4,651,727 A | | 3/1987 | Howorth | 128/201.23 |
| 4,653,120 A | | 3/1987 | Leaf | 2/114 |
| 4,696,066 A | * | 9/1987 | Ball et al. | 2/272 |
| 4,718,124 A | | 1/1988 | Sawicki et al. | 2/114 |
| 4,787,101 A | | 11/1988 | Feinberg | 2/105 |
| 4,914,752 A | | 4/1990 | Hinson et al. | 2/2 |
| 4,964,282 A | | 10/1990 | Wagner | 62/259.3 |
| 5,062,424 A | | 11/1991 | Hooker | 128/379 |
| 5,190,031 A | * | 3/1993 | Guibert et al. | 607/100 |

(Continued)

FOREIGN PATENT DOCUMENTS

| | | |
|---|---|---|
| FR | 821150 | 11/1937 |
| GB | 475811 | 11/1937 |

(Continued)

OTHER PUBLICATIONS

PCT International Publication No. WO 03/086500 A2, Oct. 23, 2003 Arizant Healthcare Inc.

(Continued)

*Primary Examiner* — Aaron Roane
(74) *Attorney, Agent, or Firm* — X. Christina Huang; Adam M. Brammwell; Terrance A. Meador

(57) ABSTRACT

A warming device for perioperative use includes a clinical garment and a convective thermal blanket supported on an inside surface of the clinical garment. A mechanism may be provided to releasably attach the thermal blanket to the clinical garment.

40 Claims, 12 Drawing Sheets

U.S. PATENT DOCUMENTS

| | | | |
|---|---|---|---|
| 5,255,390 A | 10/1993 | Gross et al. | 2/2 |
| 5,304,213 A | 4/1994 | Berke et al. | 607/104 |
| 5,360,439 A | 11/1994 | Dickerhoff et al. | 607/104 |
| 5,367,710 A | 11/1994 | Karmin | 2/114 |
| 5,411,541 A | 5/1995 | Bell et al. | 607/104 |
| 5,443,488 A | 8/1995 | Namenye et al. | 607/104 |
| D362,507 S | 9/1995 | Zuck et al. | D24/206 |
| 5,515,543 A * | 5/1996 | Gioello | 2/69 |
| 5,572,742 A | 11/1996 | McFadden | 2/114 |
| 5,575,006 A | 11/1996 | Wolfe | 2/114 |
| 5,611,087 A | 3/1997 | Adkins | 2/114 |
| 5,620,482 A | 4/1997 | Augustine et al. | 607/107 |
| 5,697,963 A | 12/1997 | Augustine | 607/108 |
| 5,733,318 A | 3/1998 | Augustine | 607/104 |
| 5,749,109 A | 5/1998 | Kappel | 5/423 |
| 5,785,716 A | 7/1998 | Bayron et al. | 607/108 |
| 5,792,216 A | 8/1998 | Kappel | 607/107 |
| 5,891,187 A | 4/1999 | Winthrop et al. | 607/96 |
| 5,946,722 A | 9/1999 | Trautmann | 2/83 |
| 5,970,519 A | 10/1999 | Weber | 2/81 |
| 5,974,605 A | 11/1999 | Dickerhoff et al. | 5/421 |
| 6,049,907 A | 4/2000 | Palomo | 2/51 |
| 6,154,883 A | 12/2000 | Spann et al. | 2/69 |
| 6,156,058 A * | 12/2000 | Kappel et al. | 607/107 |
| 6,203,567 B1 | 3/2001 | Augustine | 607/104 |
| 6,216,270 B1 | 4/2001 | Moquin et al. | 2/69 |
| 6,235,659 B1 | 5/2001 | McAmish et al. | 442/79 |
| 6,260,201 B1 * | 7/2001 | Rankin | 2/69 |
| 6,378,136 B2 | 4/2002 | Matsushita | 2/114 |
| 6,484,321 B1 | 11/2002 | Shamam | 2/114 |
| 6,511,501 B1 | 1/2003 | Augustine et al. | 607/104 |
| 6,524,332 B1 | 2/2003 | Augustine et al. | 607/107 |
| 6,551,347 B1 * | 4/2003 | Elkins | 607/104 |
| 6,571,574 B1 | 6/2003 | Blackstone | 62/420 |
| 6,596,019 B2 | 7/2003 | Turner et al. | 607/108 |
| 6,647,552 B1 | 11/2003 | Hogan | 2/114 |
| 6,694,522 B1 | 2/2004 | Neal | 2/114 |
| 6,792,622 B2 | 9/2004 | Graves | 2/114 |
| 6,799,332 B2 | 10/2004 | Hatton | 2/114 |
| 6,820,622 B1 | 11/2004 | Teves et al. | 128/849 |
| 6,851,125 B2 | 2/2005 | Fujikawa et al. | 2/51 |
| 6,876,884 B2 * | 4/2005 | Hansen et al. | 607/98 |
| 7,001,416 B2 | 2/2006 | Augustine et al. | 607/104 |
| 7,226,454 B2 | 6/2007 | Albrecht et al. | 607/104 |
| 7,276,076 B2 | 10/2007 | Bieberich | 607/108 |
| 7,364,584 B2 | 4/2008 | Anderson | 607/108 |
| 7,470,280 B2 | 12/2008 | Bieberich | 607/104 |
| 2003/0126668 A1 | 7/2003 | Scroggins | 2/114 |
| 2004/0204748 A1 | 10/2004 | Hansen et al. | 607/98 |
| 2005/0015127 A1 | 1/2005 | Bieberich | 607/104 |
| 2005/0143796 A1 | 6/2005 | Augustine et al. | 607/104 |
| 2006/0047332 A1 | 3/2006 | Malmberg et al. | 607/104 |
| 2006/0122671 A1 | 6/2006 | Albrecht et al. | 607/104 |
| 2006/0122672 A1 | 6/2006 | Anderson | 607/104 |
| 2006/0147320 A1 | 7/2006 | Hansen et al. | 417/313 |
| 2006/0184216 A1 | 8/2006 | Van Duren | 607/104 |
| 2006/0184217 A1 | 8/2006 | Van Duren | 607/104 |
| 2006/0184218 A1 | 8/2006 | Bieberich | 607/104 |
| 2006/0259104 A1 | 11/2006 | Panser et al. | 607/104 |
| 2007/0093882 A1 | 4/2007 | Anderson et al. | 607/104 |
| 2007/0093883 A1 | 4/2007 | Anderson et al. | 607/104 |
| 2007/0093884 A1 | 4/2007 | Anderson et al. | 607/104 |
| 2007/0093885 A1 | 4/2007 | Anderson et al. | 607/104 |
| 2007/0239239 A1 | 10/2007 | Albrecht et al. | 607/96 |
| 2008/0027521 A1 | 1/2008 | Bieberich | 607/96 |
| 2008/0027522 A1 | 1/2008 | Bieberich | 607/96 |
| 2008/0125840 A1 | 5/2008 | Anderson | 607/104 |
| 2008/0177361 A1 | 7/2008 | Anderson | 607/108 |
| 2009/0062891 A1 | 3/2009 | Bieberich | 607/104 |
| 2009/0149931 A9 | 6/2009 | Anderson | 607/104 |
| 2009/0228083 A1 | 9/2009 | Anderson et al. | 607/107 |

FOREIGN PATENT DOCUMENTS

| | | |
|---|---|---|
| GB | 1 462 033 | 1/1997 |
| SE | 525 415 | 2/2005 |
| WO | WO 97/14381 A1 | 4/1997 |
| WO | WO 98/48652 | 11/1998 |
| WO | WO 00/62726 | 10/2000 |
| WO | WO 03/086500 A3 | 10/2003 |
| WO | WO 03/106897 A3 | 12/2003 |
| WO | WO 2004/004500 A1 | 1/2004 |
| WO | 2004/047884 A2 | 6/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006086587 A1 | 8/2006 |
| WO | WO 2007/047917 A1 | 4/2007 |
| WO | WO 2008/013603 | 1/2008 |
| WO | WO 2008/091486 | 7/2008 |

OTHER PUBLICATIONS

P.O. Fanger, Thermal Comfort: Analysis and Applications in Environmental Engineering, Danish Technical Press, 1970, pp. 5-67.
C.B. Mahony & J. Odom, Maintaining intraoperative normothermia: A meta-analysis of outcomes with costs. *AANA Journal*. Apr. 1999. v. 67, No. 2:155-164.
Porta-Chill—The Portable Air-Chiller—Brochure, http://www.portachil.com/, Dec. 3, 2002.
EPO Examination Report mailed Oct. 24, 2006, in EP03719690.4-1526, EP Regional Phase of PCT/US2003/11128 (published as WO/2003/086500).
International Search Report and Written Opinion in PCT/US2006/004644, mailed Dec. 18, 2006.
Written Opinion of the International Search Authority (EPO) in PCT/US2006/041028, mailed Feb. 20, 2007.
Non-Final Office Action in U.S. Appl. No. 11/006,491, mailed Aug. 17, 2007.
Examiner's Report in EP 03719690, mailed Dec. 17, 2007.
International Search Report and Written Opinion in PCT/US2005/025355, mailed Dec. 1, 2005.
International Search Report and Written Opinion in PCT/US2005/043968, mailed Apr. 19, 2006.
International Search Report and Written Opinion in PCT/US2005/044214, mailed Apr. 19, 2006.
International Search Report and Written Opinion in PCT/US2007/013073, mailed Nov. 9, 2007.
EPO Examination Report mailed Sep. 2, 2008, in EP05789978.3, EP Regional Phase of PCT/US2005/025355 (published as WO/2006/020170).
EPO Examination Report mailed Jan. 23, 2009, in EP05853202, EP Regional Phase of PCT/US2005/044214 (published as WO/2006/063027).
International Search Report and Written Opinion in PCT/US2008/000141, mailed Nov. 11, 2008.
Snuggle Warm® Tube Blanket, SMiths Medical, © 2005, two pages.
Brauer A, et al., Comparison of forced-air warming systems with upper body blankets using a manikin of the human body. *Acta Anaesthesiologica Scandanavica*: 2002: 46: 965-972.
EPO Examination Report mailed Sep. 29, 2009, in EP06720577.3.
EPO Examination Report mailed Jun. 22, 2009, in EP05853202.9.
EPO Examination Report mailed May 24, 2009, in EP06826351.6.
Response to 1$^{st}$ EPO Examination Report in EP06720577.3, submitted Mar. 23, 2010.
Response to 1$^{st}$ EPO Examination Report in EP06826351.6, submitted Aug. 20, 2009.
2$^{nd}$ EPO Examination Report in EP06826351.6, submitted Apr. 14, 2010.
Response to 2$^{nd}$ EPO Examination Report in EP06826351.6, submitted Aug. 13, 2010.

* cited by examiner

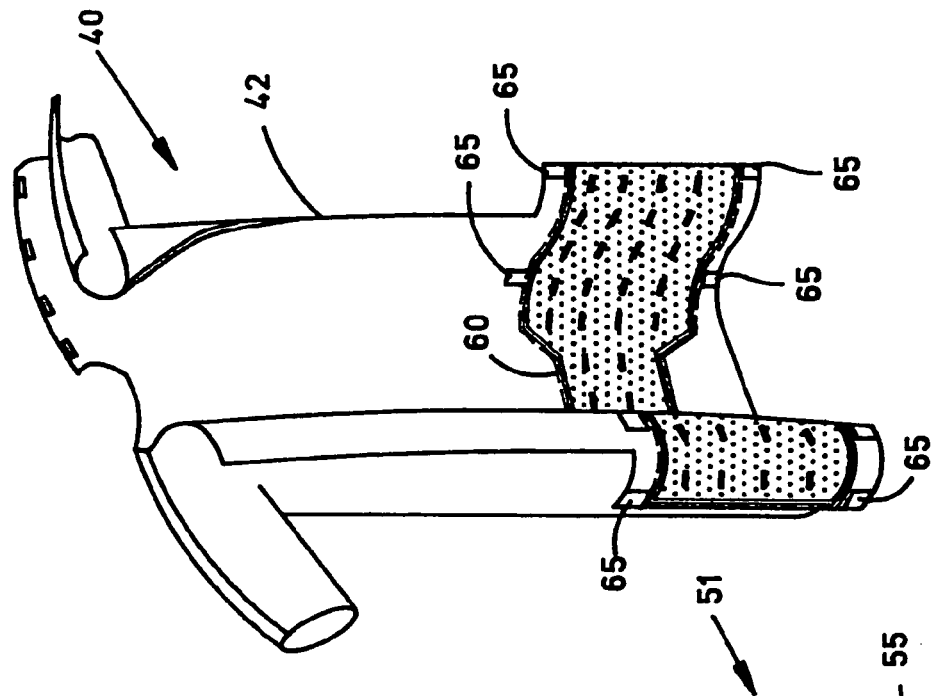
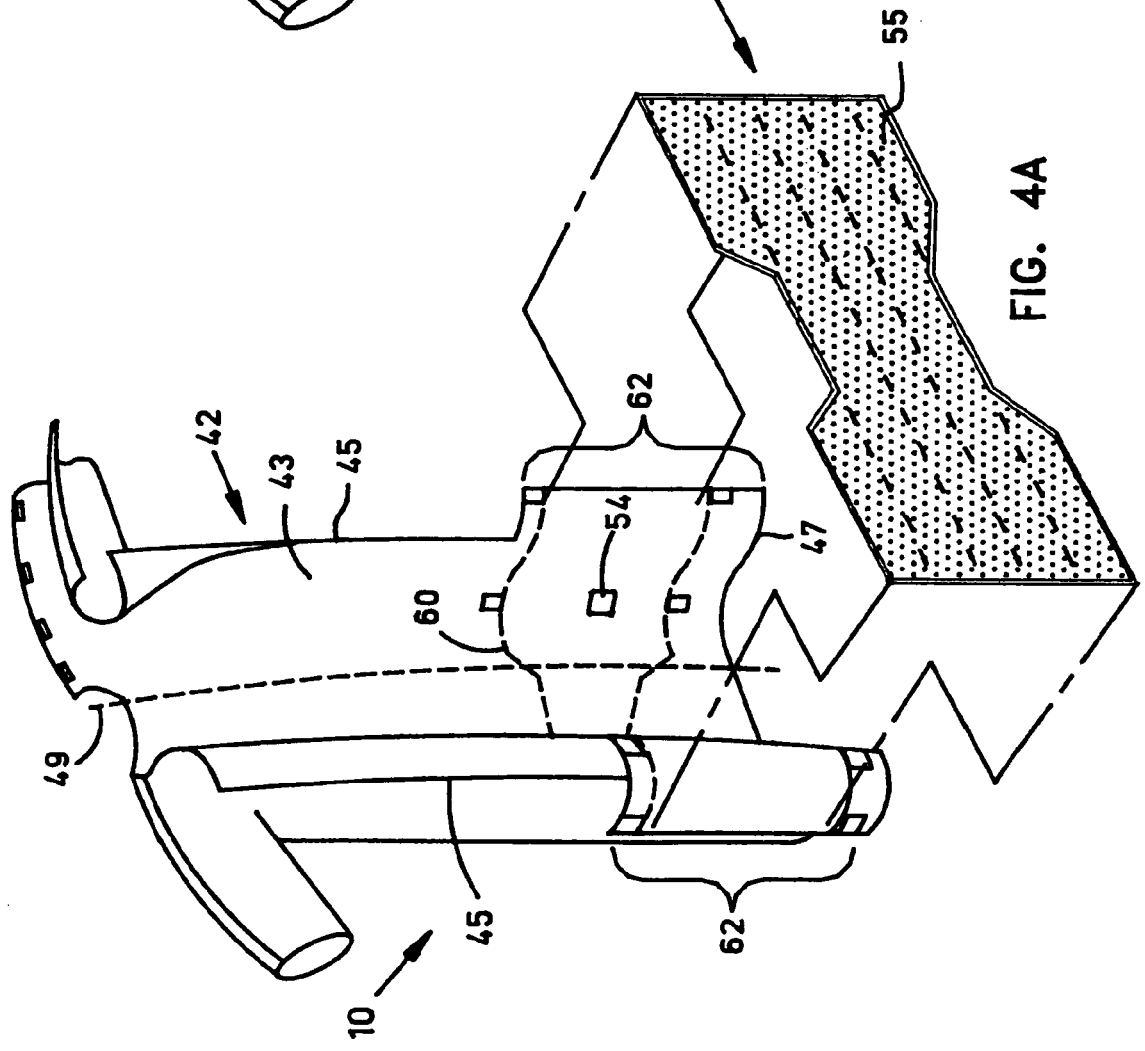
FIG. 4A
FIG. 4B

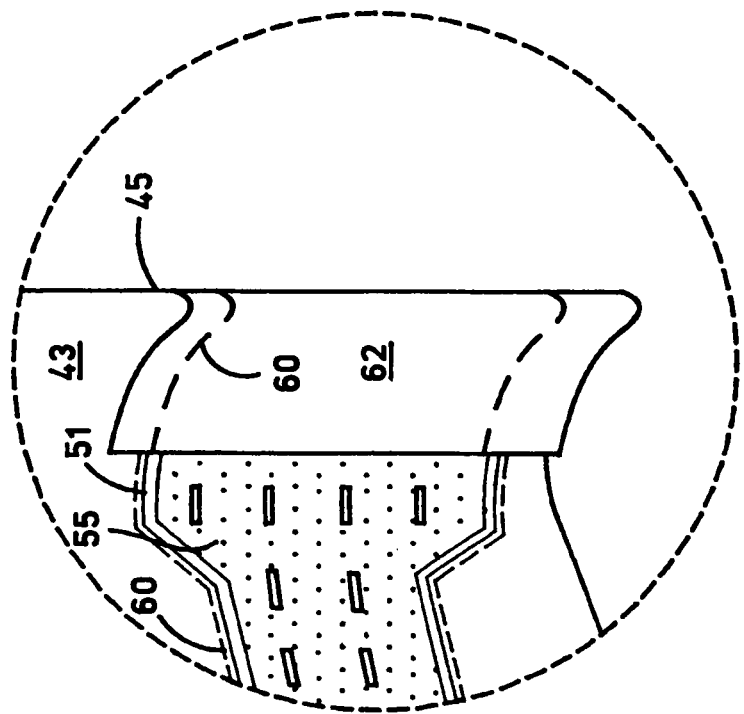
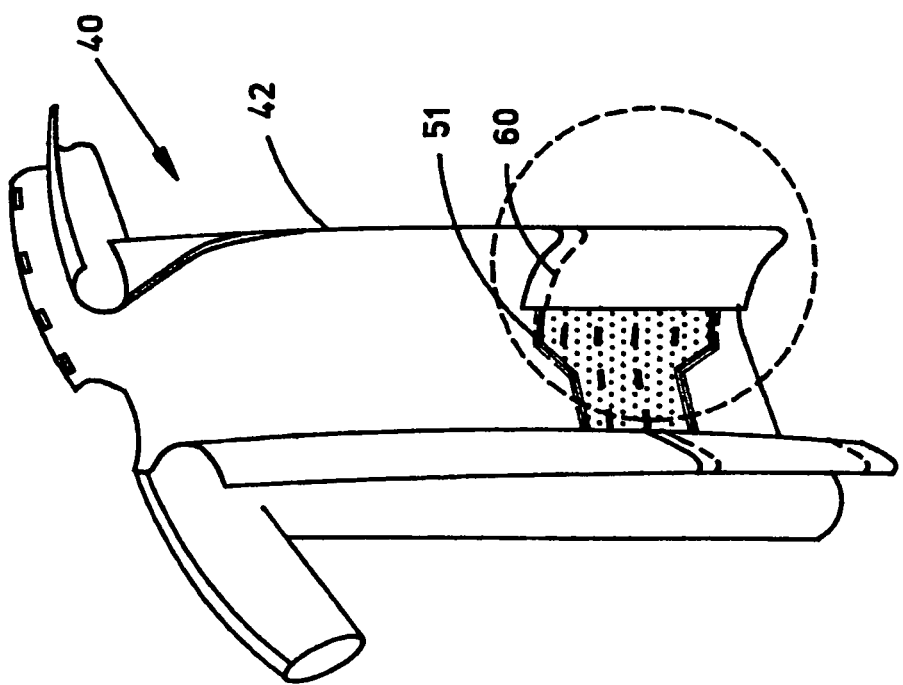
FIG. 4D
FIG. 4C

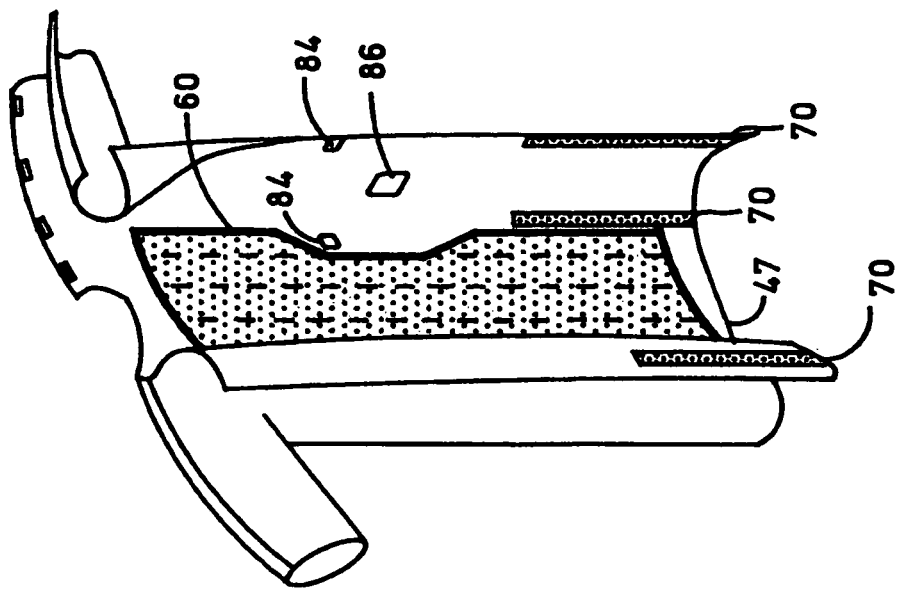
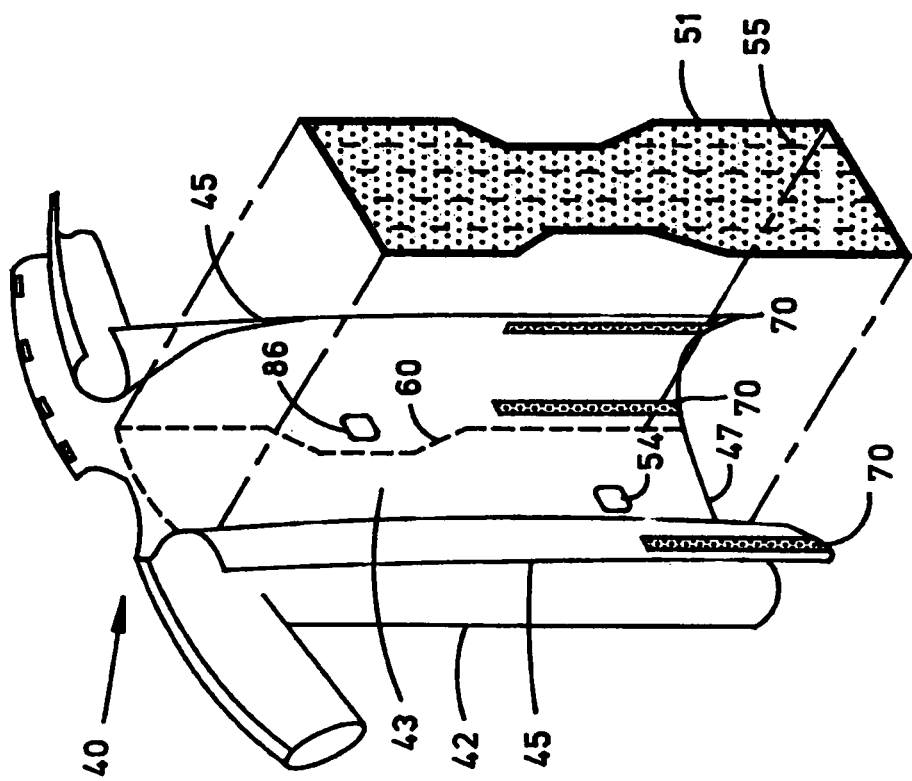

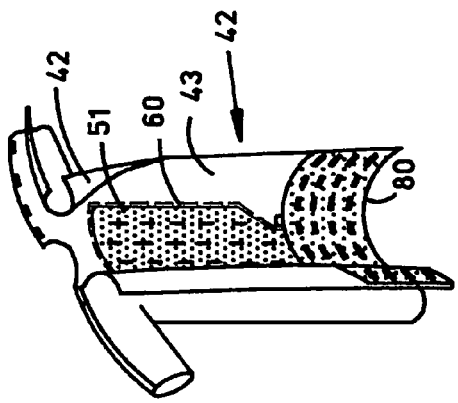
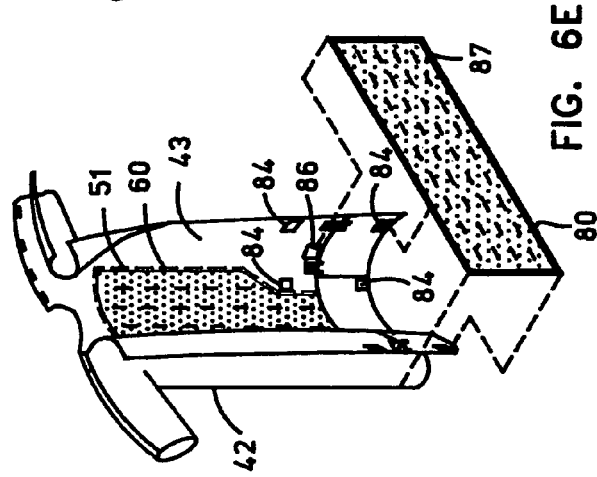
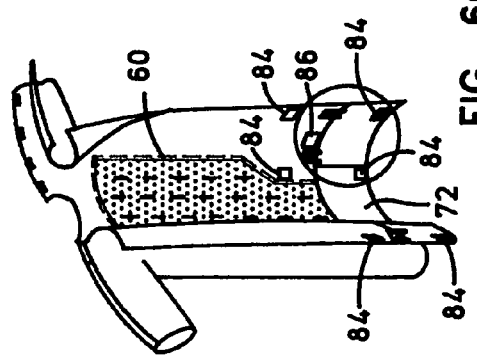
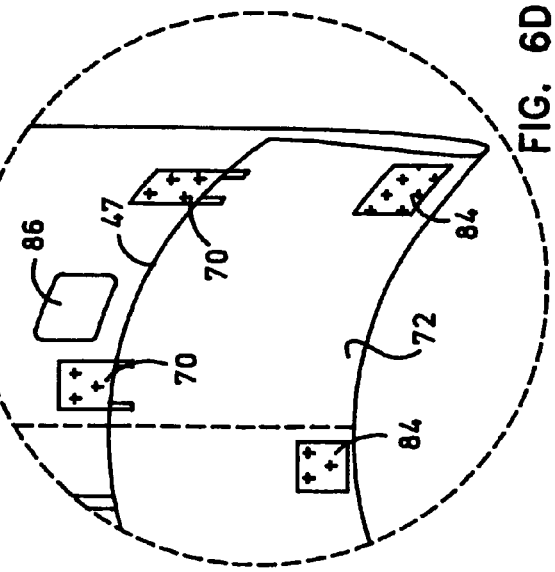

WARMING DEVICE FOR PERIOPERATIVE USE

RELATED APPLICATIONS

This application contains subject matter related to the subject matter of the following patent applications, all commonly owned herewith:

Patent Cooperation Treaty (PCT) Application No. PCT/US2003/11128, filed Apr. 10, 2003, entitled "Patient Comfort Apparatus and System", and published on Oct. 23, 2003 under Publication No. WO 2003/086500;

Patent Cooperation Treaty (PCT) Application No. PCT/US2005/025355, filed Jul. 18, 2005, entitled "Perioperative Warming Device", and published on Feb. 23, 2006 under Publication No. WO 2006/020170;

Patent Cooperation Treaty (PCT) Application No. PCT/US2005/043968, filed Dec. 6, 2005, entitled "Warming Device with Varied Permeability", and published on Jun. 15, 2006 under Publication No. WO 2006/062910;

Patent Cooperation Treaty (PCT) Application No. PCT/US2005/044214, filed Dec. 6, 2005, entitled "Warming Device", and published on Jun. 15, 2006 under Publication No. WO 2006/063027;

Patent Cooperation Treaty (PCT) Application No. PCT/US2006/004644, filed Feb. 9, 2006, entitled "Warming Device for Perioperative Use", and published on Aug. 17, 2006 under Publication No. WO2006/086587;

PCT Application No. PCT/US2006/041028, filed Oct. 19, 2006, entitled "Multifunction Warming Device for Perioperative Use", and published on Apr. 26, 2007 under Publication No. WO 2007/047917;

PCT Application No. PCT/US2007/013073, filed Jun. 1, 2007, entitled "Warming Device", and published on Jan. 31, 2008 under Publication No. WO2008/013603;

PCT Application No. PCT/US2008/000141, filed Jan. 4, 2008, entitled "Convective Warming Device With a Drape" and published on Jul. 31, 2008 under Publication No. WO 2008/091486;

U.S. patent application Ser. No. 10/411,865, filed Apr. 10, 2003, entitled "Patient Comfort Apparatus and System" and published on Oct. 16, 2003 under Publication No. US 2003/0195596, now U.S. Pat. No. 7,001,416;

U.S. patent application Ser. No. 10/508,319, 371(c) date Mar. 3, 2005, entitled "Patient Comfort Apparatus and System" and published on Jun. 30, 2005 under Publication No. US 2005/0143796;

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 11/005,883, filed Dec. 7, 2004, entitled "Warming Device with Varied Permeability" and published on Jun. 8, 2006 under Publication No. US 2006/0122671, now U.S. Pat. No. 7,226,454;

U.S. patent application Ser. No. 11/006,491, filed Dec. 7, 2004, entitled "Warming Device" and published on Jun. 8, 2006 under Publication No. US 2006/0122672, now U.S. Pat. No. 7,364,584;

U.S. patent application Ser. No. 11/057,396, filed Feb. 11, 2005, entitled "Perioperative Warming Device", and published on Aug. 17, 2006 under Publication No. US 2006/0184215, now U.S. Pat. No. 7,276,076;

U.S. patent application Ser. No. 11/057,397, filed Feb. 11, 2005, entitled "Thermal Blanket for Warming the Limbs," published on Aug. 17, 2006 under Publication No. US 2006/0184216;

U.S. patent application Ser. No. 11/057,404, filed Feb. 11, 2005, entitled "Clinical Garment for Comfort Warming and Prewarming," published on Aug. 17, 2006 under Publication No. US 2006/0184218;

U.S. patent application Ser. No. 11/260,706, filed Oct. 27, 2005, entitled "Patient Comfort Apparatus and System", and published on Mar. 9, 2006 under Publication No. US 2006/0052853;

U.S. patent application Ser. No. 11/363,136, filed Feb. 27, 2006, entitled "Forced Air Warming Unit" and published on Jul. 6, 2006 under Publication No. US 2006/0147320;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/583,432, filed Oct. 19, 2006, entitled "Multifunction Warming Device for Perioperative Use", and published on Apr. 26, 2007 under Publication No. US 2007/0093882;

U.S. patent application Ser. No. 11/583,477, filed Oct. 19, 2006, entitled "Multifunction Warming Device with Provision for Being Secured", and published on Apr. 26, 2007 under Publication No. US 2007/0093883;

U.S. patent application Ser. No. 11/583,480, filed Oct. 19, 2006, entitled "Multifunction Warming Device with Provision for Warming Hands", and published on Apr. 26, 2007 under Publication No. US 2007/0093884;

U.S. patent application Ser. No. 11/583,481, filed Oct. 19, 2006, entitled "Multifunction Warming Device with an Upper Body Convective Apparatus", and published on Apr. 26, 2007 under Publication No. US 2007/0093885;

U.S. patent application Ser. No. 11/656,777, filed Jan. 23, 2007, entitled "Convective Warming Device With a Drape";

U.S. patent application Ser. No. 11/704,547, filed Feb. 9, 2007, entitled "A Forced Air Warming Unit";

U.S. patent application Ser. No. 11/801,292, filed May 9, 2007, entitled "Warming Device with Varied Permeability", and published on Oct. 11, 2007 under Publication No. US 2007/0239239;

U.S. patent application Ser. No. 11/899,872, filed Sep. 7, 2007, entitled "Perioperative Warming Method", and published on Jan. 31, 2008 under Publication No. US 2008/0027522; and, U.S. patent application Ser. No. 11/899,928, filed Sep. 7, 2007, entitled "Perioperative Warming Device", and published on Jan. 31, 2008 under Publication No. US 2008/0027521.

BACKGROUND OF THE INVENTION

A warming device for perioperative use includes a clinical garment with one or more convective thermal blankets supported on the inside of the garment.

Convective devices that transfer heat to a human body are known. For example, there are devices that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These devices are typically called "convective thermal blankets" or "covers"; for convenience, in this discussion and the following specification, they shall be called, simply, "thermal blankets." Arizant Healthcare Inc., the assignee of this application, makes and sells such devices under the BAIR HUGGER® brand. One such device is the Model 522 Upper Body Blanket.

Use of the term "convective" to denote the transfer of heat between the warming device and a body refers to the principal mode of heat transfer, it being understood that heat may at the same time be transferred between a warming device and a body by conduction and radiation, although not to the degree of convection.

A recent invention disclosed in the referenced PCT application adapts a clinical garment such as a robe or gown to receive a convective device in order to warm a person wearing the garment in a clinical setting for comfort and mobility of the person. There is a need to further adapt such a combination for use perioperatively.

The term "perioperative" is defined in the *PDR Medical Dictionary*, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. *AANA Journal.* 4/99; 67, 2:155-164.), therapeutic warming is employed during at least the intraoperative period in order to prevent or mitigate a constellation of effects that result from hypothermia. In fact, it is increasingly manifest that maintenance of normothermia perioperatively enhances the prospects for a quick, successful recovery from surgery. The effectiveness of therapeutic warming depends upon delivery of enough heat to a patient's body to raise the patient's core body temperature to, or maintain it within, a narrow range, typically near 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort". Of course, therapeutic warming may also comfort a patient by alleviating shivering or a feeling of being cold, but this is a secondary or ancillary effect. Thermal comfort is a subjective notion; however, the environmental conditions necessary to produce a sense of thermal comfort in a population of human beings are known and well tabulated. For example, Fanger (*Thermal Comfort: Analysis and Applications of Environmental Engineering*. Danish Technical press, Copenhagen, 1970) defines thermal comfort as "that condition of mind which expresses satisfaction with the thermal environment." Even when a patient is normothermic, less than ideal environmental conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Therapeutic warming may be indicated during any one or more of the perioperative periods. For example, for a short operation in a surgery with no warming equipment available, a person may be warmed preoperatively in a preparation area to raise mean body temperature to a level higher than normal in order to store enough thermal energy to maintain normothermia, without heating, intraoperatively. After surgery, it may be necessary to apply therapeutic warming in a recovery area to raise the core temperature to normothermia and maintain it there for a period of time while anesthesia wears off. Alternatively, for a long surgery in an arena with heating equipment available, a person may be warmed for comfort before surgery and warmed therapeutically during and after surgery.

Both therapeutic warming and comfort warming may be provided by convective devices such as convective thermal blankets that receive and distribute warmed, pressurized air and then expel the distributed air through one or more surfaces toward a patient in order to prevent or treat hypothermia in the patient. An example of use of such a device for therapeutic warming is found in U.S. Pat. No. 6,524,332, "System and Method for Warming a Person to Prevent or Treat Hypothermia", commonly owned with this application. Comfort warming by convective means is described in the referenced U.S. Patent Application, and the referenced Publication No. WO 03/086500.

When delivered by convective devices, therapeutic warming is distinguished from comfort warming by intended effects and by the parameters of heat delivery that produce those effects. In this regard, a convective warming system typically includes a source of warmed pressurized air (also called a heater/blower unit, a forced air warming unit, a heater unit, etc.), a convective device such as a thermal blanket (which is, typically, inflatable), and a flexible conduit or air hose connecting the heater/blower unit with the thermal blanket. Use of such a system for a particular type of warming requires delivery of warmed air through a thermal blanket at parametric values that achieve a particular objective. The conditions by which a convective device such as a thermal blanket produces thermal comfort in normothermic individuals at steady state are significantly different from those necessary to treat hypothermia. Typically the conditions for thermal comfort are met in a system with a relatively low capacity heater/blower unit, while those in a therapeutic warming system are achieved with a relatively high capacity heater/blower unit. The different capacities have led to use of air hoses with different capacities, with those delivering air flow for thermal comfort typically having smaller diameters than those serving a therapeutic warming requirement. The result is a divergence of designs leading to installation of different air delivery infrastructures for therapeutic and comfort warming.

Health care cost is an issue of national importance. The cost of warming perioperatively is directly related to the number of perioperative periods in which a person is warmed; the cost increases when different warming apparatus are used in different periods to accomplish different goals. For example, when comfort and mobility are objectives of warming a person during the preoperative period and therapy is the objective of warming during one or more of the intraoperative and postoperative periods, it is presently necessary to use different warming configurations. Manifestly, if one warming device could be used or adapted to be used perioperatively, significant savings in thermal care could be realized.

SUMMARY OF THE INVENTION

In one aspect, a warming device includes a clinical garment having an inside surface supporting a convective thermal blanket.

In another aspect, a warming device includes a clinical garment and a convective thermal blanket releasably attached to the inside of the garment.

In yet another aspect, a convective thermal blanket is adapted to be released from a clinical garment used for preoperative warming in order to be deployed for therapeutic warming intraoperatively.

BRIEF DESCRIPTION OF THE DRAWINGS

FIGS. 4A-4D are perspective drawings showing assembly of a warming device constituted of a clinical garment with flaps and an upper body thermal blanket disposed transversely across the inside of the garment, between the flaps.

FIGS. 6A-6F are perspective drawings showing assembly of a warming device constituted of a clinical garment with a lower hem and an upper body thermal blanket disposed longitudinally along the inside of the garment. FIGS. 6E and 6F also show a second thermal blanket disposed transversely across the inside of the garment, over a portion of the upper body thermal blanket.

FIGS. 7A and 7B also show a second thermal blanket disposed transversely across the inside of the garment, between the lower hem and the upper body thermal blanket.

SPECIFICATION

A warming device is constituted of a clinical garment and at least one thermal blanket supported on an inside surface of the garment. In this regard, a "clinical garment" is a garment that is typically used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. The thermal blanket receives and distributes at least one stream of warmed pressurized air in a structure for being disposed on, adjacent, or next to the core and/or the limbs of a body. When pressurized with warmed air, the thermal blanket emits warmed air through one or more of its surfaces. The thermal blanket may be releasably attached to the inside surface of the garment.

In one aspect, a warming device for perioperative use may be worn on a person where it receives a stream of warmed pressurized air, distributes the pressurized air within the attached thermal blanket, and emits the air through one or more surfaces of the thermal blanket to warm the person's body. In another aspect, the warming device may be adapted for therapeutic warming during surgery. In yet another aspect, the warming device may be adapted for therapeutic warming by detaching the thermal blanket from the clinical garment for deployment intraoperatively. In yet another aspect, the thermal blanket may be reattached to the clinical garment for further use on the same person during the postoperative period. Various illustrative versions of the warming device are illustrated and discussed in this specification.

In the warming device illustrated and discussed below, the thermal blankets are inflatable. That is, their structures, flaccid when not in use, tauten when receiving a stream of pressurized air.

Figure 1:
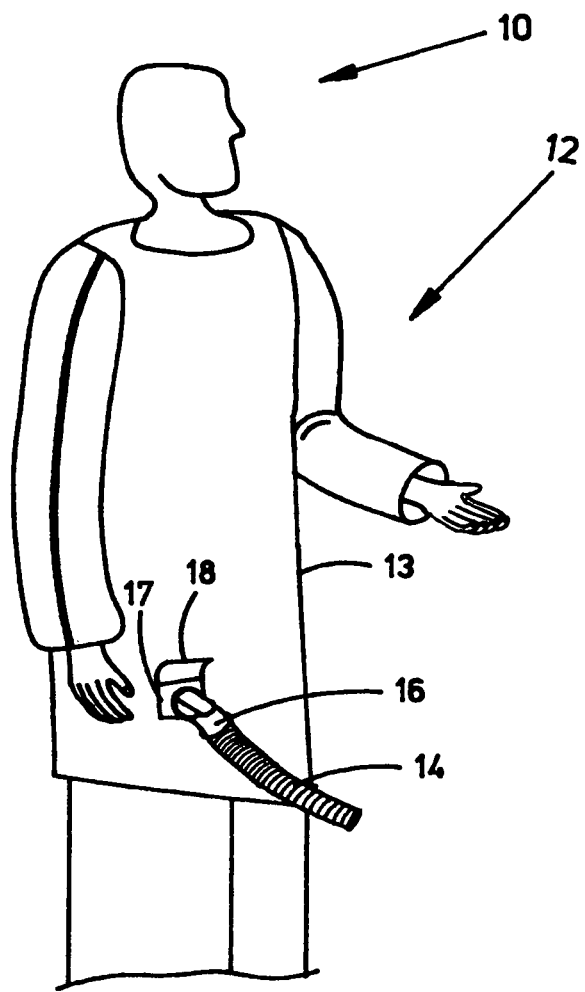
FIG. 1 is an illustration of a person wearing a warming device constituted of a clinical garment and a thermal blanket mounted to the inside of the garment.

Refer now to the figures, in which a person 10 wearing a warming device 12 for perioperative use is illustrated in FIG. 1. The warming device 12 is constituted of a clinical garment 13 and at least one thermal blanket (not seen in this view) that is supported on an inside surface of the clinical garment 13. Further, the thermal blanket may be detachable from the garment. In this specification, the term "detachable" may also mean releasable or separable. The thermal blanket receives warmed, pressurized air from a heater/blower unit (not seen in this view) through an air hose 14 with a nozzle 16 that is received in an inlet port 17 of the thermal blanket. The inlet port may be accessed through a flap 18 in the garment.

Figure 2A:
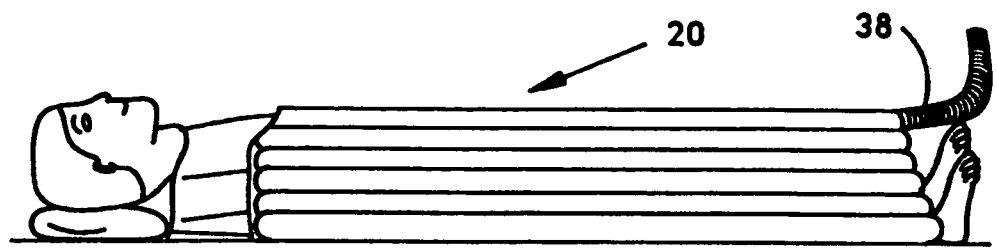
FIGS. 2A-2D are illustrations of full body, lower body, and upper body convective thermal blankets.
Figure 2B:
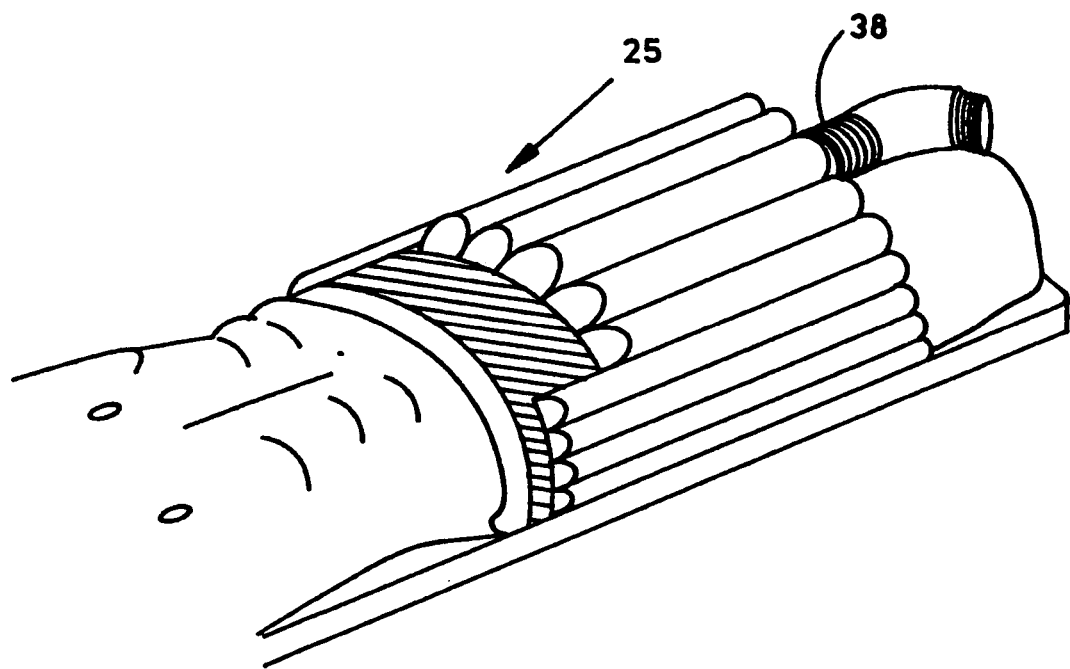
Figure 2C:
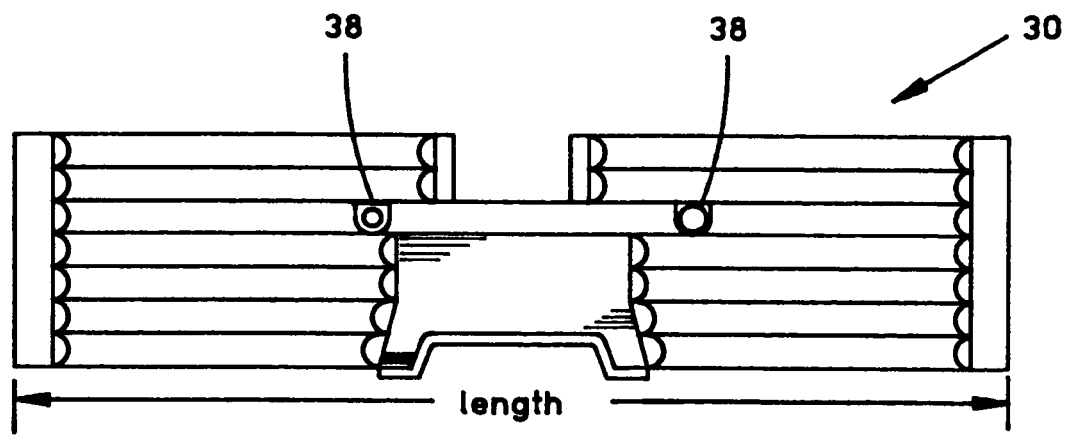
Figure 2D:
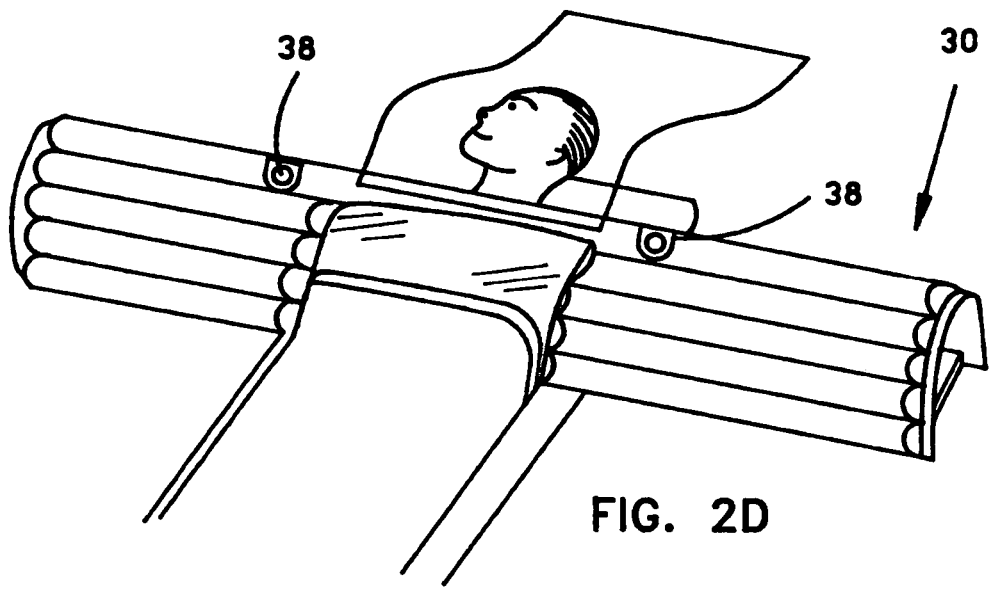

Thermal blankets have been specifically designed for particular deployments. Three representative thermal blankets are shown in FIGS. 2A-2D. A "full body" thermal blanket 20 is shown in FIG. 2A. The full body thermal blanket is adapted to lie upon the person and to extend longitudinally along the body of the person in order to cover substantially the person's entire body, from near the ankles or feet up to the neck. A "lower body" thermal blanket 25 is shown in FIG. 2B. The lower body thermal blanket 25 is adapted to lie upon the person and to extend longitudinally along the body of a person in order to cover the person's lower body, from near the ankles or feet up to the waist or pelvis of the person. An upper body thermal blanket 30 is illustrated in FIGS. 2C and 2D. The upper body thermal blanket 30 has a bow-tie shape that is adapted to lie upon and extend transversely across the upper body of a person in order to cover the person's chest and extended arms. When fed a stream of warmed pressurized air, each of the thermal blankets 20, 25, 30 inflates and distributes the air within itself. The pressurized air flows through apertures on the surface of the thermal blanket which faces the person. These thermal blankets may have one, two, or more inlet ports 38 through which an air hose provides warmed pressurized air from a heater/blower unit (not shown in these drawings). The construction of thermal blankets is well understood. Examples of specific constructions are given in the referenced Publication No. WO 03/086500 and in U.S. Pat. No. 5,620,482, U.S. Pat. No. 5,443,488, U.S. Pat. No. 5,360,439, and U.S. Pat. No. 5,304,213.

The upper body thermal blanket 30 shown in FIGS. 2C and 2D is frequently used during thoracic, abdominal and pelvic surgery when a patient's core body temperature can drop to hypothermic levels quickly. To prevent or mitigate the effects of hypothermia an upper body blanket is deployed for therapeutic warming during the intraoperative period and may be deployed during the postoperative period for therapeutic or comfort warming. Preceding such surgery the patient may be treated with comfort warming. If warmed preoperatively with one of the comfort warming devices described in the referenced Publication No. WO 03/086500, the clinical garment must be removed when the patient is moved to surgery in order to maximize access to the surgical site. At the same time, an upper body thermal blanket must be unpackaged, made ready and deployed. A clinical garment may be indicated for postoperative warming. Similar considerations attend use of the lower body thermal blanket 25 for surgery on the head, arm, face, or neck. Manifestly, a substantial convenience and a significant reduction in cost would result from perioperative use of a single warming device capable of providing comfort warming preoperatively, therapeutic warming intraoperatively, and optional therapeutic or comfort warming postoperatively.

Such a warming device is constituted of a clinical garment and a thermal blanket supported on an inside surface of the garment. The thermal blanket may be permanently attached to the inside surface, or may be removable therefrom. If the thermal blanket is removable, the warming device may be further constituted of a mechanism acting between the garment and the thermal blanket and adapted to detach the thermal blanket from the garment. With the thermal blanket attached inside the garment, the device can be worn by the patient and comfort warming can be provided. In preparation for surgery, the thermal blanket can be left on the warming garment while the garment is folded over or around the thermal blanket so that the thermal blanket may be deployed on the patient for therapeutic warming during surgery. In this case, the clinical garment may be unfolded to be again worn by the patient or to act as a blanket or drape while the patient is therapeutically warmed postoperatively. Alternatively, the thermal blanket may be detached, removed, or otherwise separated from the garment and deployed on the patient for therapeutic warming. In some instances if the thermal blanket is detached, the thermal blanket may be reattached to the clinical garment for further use postoperatively on the same patient. In other instances, one or more additional thermal blankets can be provided inside the garment.

Figure 3B:
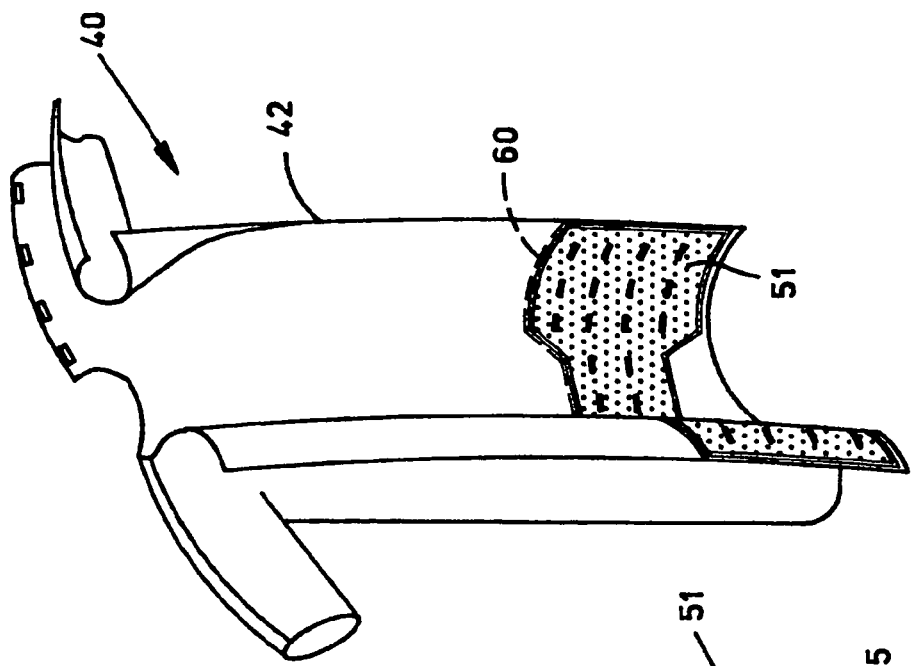
FIGS. 3A and 3B are perspective assembly drawings of a warming device constituted of a clinical garment and an upper body thermal blanket disposed transversely across the inside of the garment.
Figure 3A:
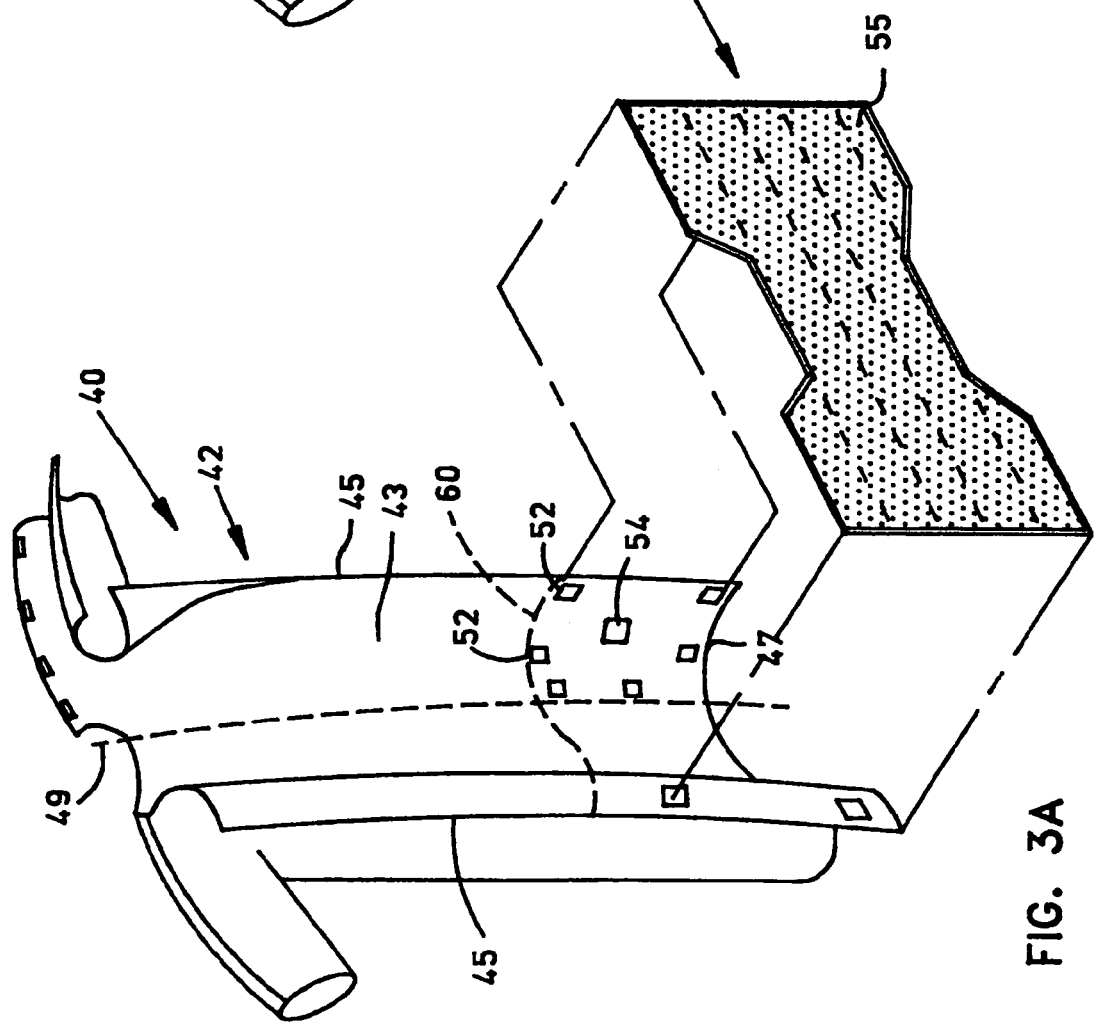

FIGS. 3A and 3B illustrate a warming device 40 for perioperative use. The warming device 40 is constituted of a clinical garment 42 with an inside surface 43, two opposing lateral hems 45, a lower hem 47, and a longitudinal axis 49. A thermal blanket is supported on the inside surface 43. For example, the thermal blanket may be an upper body thermal blanket 51 supported on the inside surface 43, transversely to the longitudinal axis of the garment 42, for example, the thermal blanket may be releasably attached to the inside surface 43. Preferably, the upper body thermal blanket 51 is positioned in a lower portion of the inside of the garment 42, near or adjacent the lower hem 47. An opening 54 in the garment 42 provides access by which an air hose can connect to an inlet port of the upper body thermal blanket 51. Warmed, pressurized air flowing into the blanket exits through apertures in the surface 55. The thermal blanket 51 may be a separate piece which is attached to the garment, or it may be formed integrally with the garment in the manner disclosed, for example, in FIGS. 1D and 1E or FIGS. 3D-3F of PCT publication WO 03/086500.

In FIGS. 3A and 3B, a mechanism to releasably retain the upper body thermal blanket 51 as a separate element includes a plurality of islands 52 of pressure sensitive adhesive material, hook and eye material, snaps, or other equivalent elements on the inside surface 43. The islands 52 may be arranged in a pattern that lies on an outline of the periphery of the upper body thermal blanket 51. Corresponding elements are provided on the posterior surface of the upper body thermal blanket 51 which faces the inside surface 43 of the garment in order to engage the islands 52. With this construction, the upper body thermal blanket 51 can be detached from the garment 42 by pulling it away from the inside surface 43. In this aspect, if the gown is needed for warming during the postoperative period, the thermal blanket may be reattached to the garment by bringing the posterior surface of the thermal blanket against the pattern of islands on the inside surface 43.

In FIGS. 3A and 3B, a mechanism to releasably retain the upper body thermal blanket 51 as an element formed integrally with the garment includes perforations, lines of weakness, or any equivalent structure that allows the thermal blanket to be detached from the garment by tearing along the trace of the mechanism. Such a trace is indicated by reference numeral 60 in FIGS. 3A and 3B. With this construction, the upper body thermal blanket 51 can be detached from the garment 42 by tearing it away from the garment along the trace 60. In this case, the thermal blanket may be reattached to the garment by taping.

When worn as shown in FIG. 1, the warming device 40 of FIGS. 3A and 3B retains warmed air within the clinical garment for comfort warming preoperatively. When the patient transitions to surgery, the upper body thermal blanket 51 is detached from the garment 42 and deployed as shown in FIG. 2C for therapeutic warming. Postoperatively, the thermal blanket 51 may be used alone for therapeutic heating or reattached to the clinical garment 42 for therapeutic or comfort heating.

FIGS. 4A-4D illustrate another aspect of the warming device 40 for perioperative use, constituted as described above in connection with FIGS. 3A and 3B, with exceptions to be described. In this case, it may be that the emerging standard dimensions of the upper body thermal blanket will require adaptation of the form of the clinical garment. Typically, the length of the upper body blanket is 72 inches along the dimension shown in FIG. 2D, although the dimension may vary from 65 inches to 75 inches. In order to accommodate this length, the structure of the clinical garment 42 includes two opposed flaps 62 formed in the lower portions of the two opposed lateral hems 45. The flaps 62 extend to the lower hem 47. A thermal blanket is supported on the inside surface 43, and may be releasably attached to the inside surface 43. For example, the thermal blanket may be an upper body thermal blanket 51 disposed on the inside surface 43, transversely to the longitudinal axis of the garment 42. The thermal blanket may be a separate piece which is attached to the garment, or it may be formed integrally with the garment. Preferably, the upper body thermal blanket 51 is positioned in a lower portion of the inside of the garment 42, near the lower hem 47, extending from one flap 62 to the other. As best seen in FIGS. 4C and 4D, in order to accommodate the length of the upper body blanket 51, the flaps are folded over the ends of the thermal blanket, against the inside surface 43 of the garment. The flaps are releasably retained against the inside surface 43 by opposing islands 65 of pressure sensitive adhesive material, hook and eye material, snaps, or other equivalent elements on the inside surface above and below the thermal blanket 51. An opening 54 in the garment 42 provides access by which an air hose can connect to an inlet port of the upper body thermal blanket 51. Warmed, pressurized air flowing into the blanket exits through apertures in the surface 55.

In FIGS. 4A-4D, a mechanism to releasably retain the upper body thermal blanket 51 as a separate element may include a plurality of islands of pressure sensitive adhesive material, hook and eye material, snaps, or other equivalent elements as described above in connection with FIGS. 3A and 3B. A mechanism to releasably retain the upper body thermal blanket 51 as an element formed integrally with the garment includes the alternatives along the trace described above in connection with FIGS. 3A and 3B. In this case, the thermal blanket may be reattached to the garment by taping.

Figure 5B:
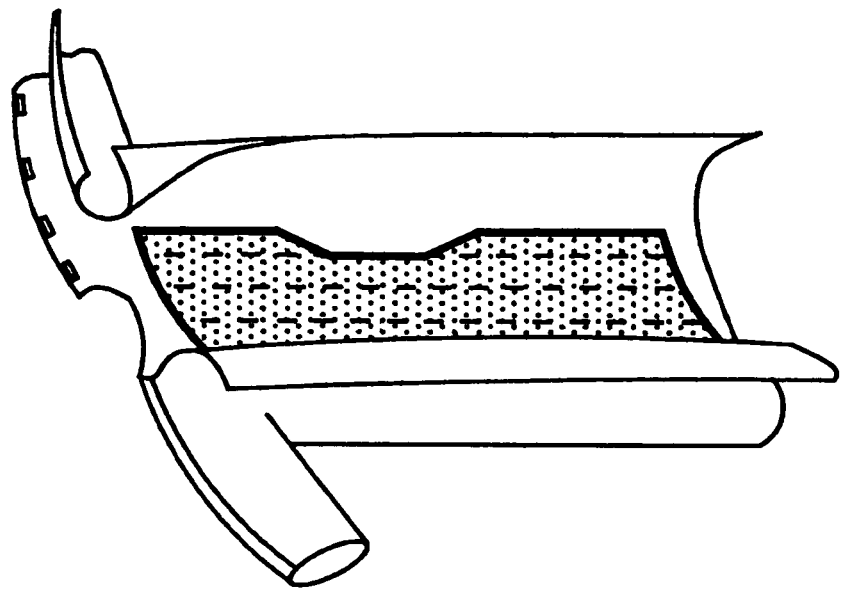
FIGS. 5A and 5B are perspective assembly drawings of a warming device constituted of a clinical garment and an upper body thermal blanket disposed longitudinally along the inside of the garment.
Figure 5A:
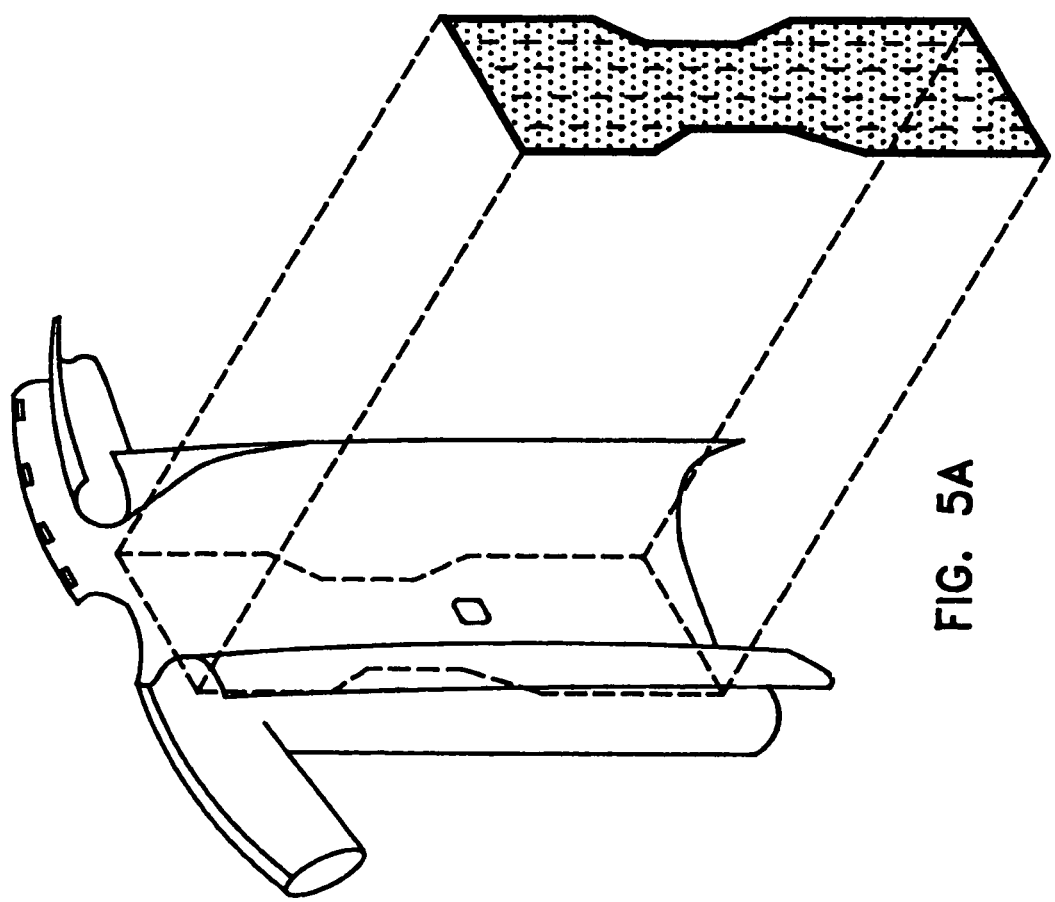

FIGS. 5A and 5B illustrate another aspect of the warming device 40 for perioperative use, constituted as described above in connection with FIGS. 3A and 3B, with exceptions to be described. In this case, the upper body thermal blanket 51 is supported on the inside surface 43, longitudinally, that is to say, in alignment with the longitudinal axis 49 of the garment 42, and may be releasably attached to the inside surface 43. Preferably, the upper body thermal blanket 51 is substantially centered in the inside of the garment 42. The thermal blanket may be a separate piece which is attached to the garment, or it may be formed integrally with the garment as described above in connection with FIGS. 3A and 3B. An opening 54 in the garment 42 provides access by which an air hose can connect to an inlet port of the upper body thermal blanket 51. Warmed, pressurized air flowing into the upper body thermal blanket 51 exits through apertures in the surface 55. A mechanism to releasably retain the upper body thermal blanket 51 as a separate element may include a plurality of islands of pressure sensitive adhesive material, hook and eye material, snaps, or other equivalent elements as described above in connection with FIGS. 3A and 3B. A mechanism to releasably retain the upper body thermal blanket 51 as an element formed integrally with the garment includes the alternatives along the trace 60 described above in connection with FIGS. 3A and 3B. In this case, the thermal blanket may be reattached to the garment by taping. When worn as shown in FIG. 1, the warming device 40 retains the warmed air within the clinical garment for comfort warming preoperatively. When the patient transitions to surgery, the upper body thermal blanket 51 is detached from the garment 42 and deployed as shown in FIG. 2C for therapeutic warming.

FIGS. 6A through 6F illustrate another aspect of the warming device 40 for perioperative use, constituted as described above in connection with FIGS. 5A and 5B, with exceptions to be described. In this case, the upper body thermal blanket 51 is longitudinally disposed on the inside surface 43, in alignment with the longitudinal axis 49 of the garment 42, and may be releasably attached to the inside surface 43. Preferably, the upper body thermal blanket 51 is substantially centered in the inside of the garment 42. The thermal blanket may be a separate piece which is attached to the garment, or it may be formed integrally with the garment as described above in connection with FIGS. 3A and 3B. An opening 54 in the garment 42 provides access by which an air hose can connect to an inlet port of the upper body thermal blanket 51. Warmed, pressurized air flowing into the upper body thermal blanket 51 exits through apertures in the surface 55.

As best seen in FIGS. 6A and 6B, a mechanism to releasably retain the upper body thermal blanket 51 as a separate element may include a plurality of islands of pressure sensitive adhesive material, hook and eye material, snaps, or other equivalent elements as described above in connection with FIGS. 3A and 3B. A mechanism to releasably retain the upper body thermal blanket 51 as an element formed integrally with the garment includes the alternatives along the trace 60 described above in connection with FIGS. 3A and 3B. In this case, the thermal blanket may be reattached to the garment by taping.

The warming garment illustrated in FIGS. 6A through 6F may have its length adjusted to accommodate the length of the upper body thermal blanket 51. In this regard, strips 70 of pressure sensitive adhesive material, hook and eye material, snaps, or other equivalent elements are attached longitudinally to the inside surface 43. The lower hem 47 may be folded upwardly over the lower end of the upper body thermal blanket 51 to the inside surface to be retained against the surface 43 by the action of the strips 70 against themselves. This shortens the length of the garment 42 by the length of the folded section 72.

As shown in FIGS. 6E and 6F, a second thermal blanket 80 may be releasably attached to the inside surface 43 of the garment over the folded section 72. For this purpose, a plurality of islands 84 of pressure sensitive adhesive material, hook and eye material, snaps, or other equivalent elements may be provided on the folded section 72 and the inside surface 43. The islands 84 may be arranged in a pattern that lies on an outline of the periphery of the thermal blanket 80. Corresponding elements may be provided on the posterior surface of the second thermal blanket 80 which faces the inside surface 43 and the folded portion 72 in order to engage the islands 84. A second opening 86 in the garment 42 provides access by which an air hose can connect to an inlet port of the second thermal blanket 80. Warmed, pressurized air flowing into the second thermal blanket 80 exits through apertures in the surface 87.

When worn as shown in FIG. 1, the warming device 40 of FIGS. 6A through 6F retains the warmed air within the clinical garment for comfort warming preoperatively. In this case, the warmed air is provided through the second thermal blanket 80. When the patient transitions to surgery, the second thermal blanket 80 is detached from the clinical garment 42, the folded portion 72 is unfolded, and the upper body thermal blanket 51 is detached from the garment 42 and deployed as shown in FIG. 2C for therapeutic warming. Postoperatively, the thermal blanket 51 may be used alone for therapeutic heating; alternatively, the upper body thermal blanket 51 or the second thermal blanket 80 may be reattached to the clinical garment 42 for therapeutic or comfort heating.

Figures 7A, 7B:
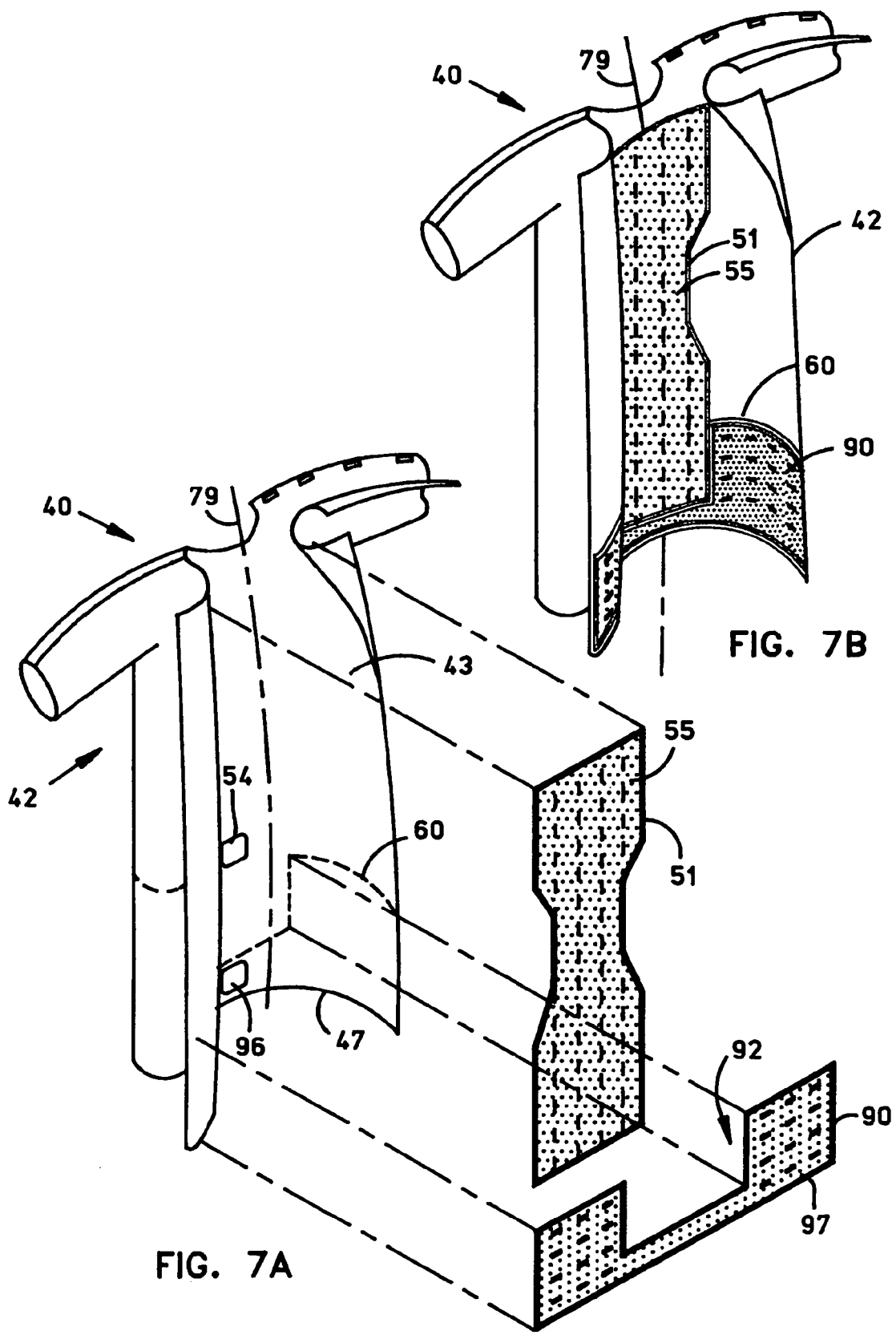
FIGS. 7A-7C are perspective drawings showing assembly of a warming device constituted of a clinical garment with a lower hem and an upper body thermal blanket disposed longitudinally along the inside of the garment.
Figure 7C:
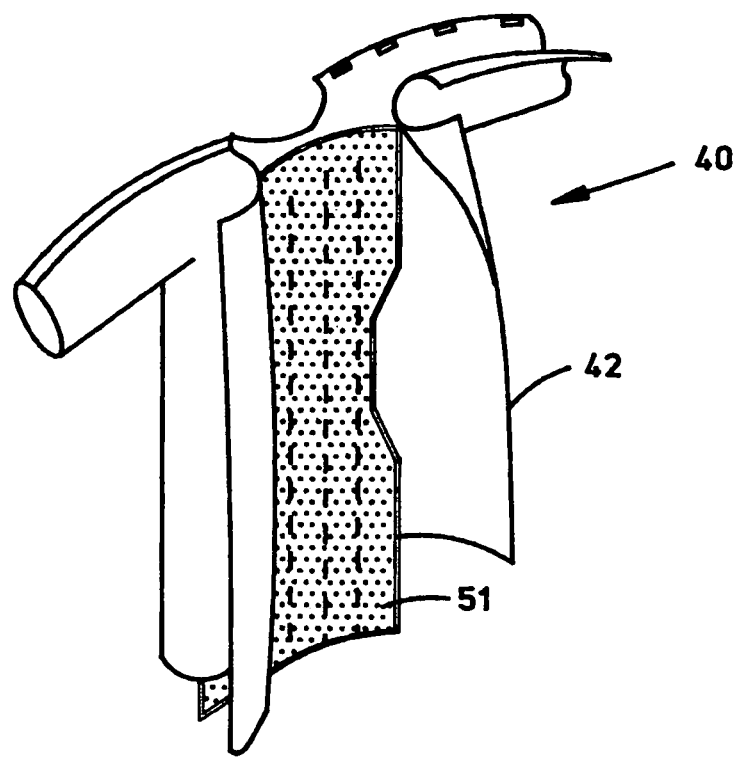

FIGS. 7A through 7C illustrate another aspect of the warming device 40 for perioperative use, constituted as described above in connection with FIGS. 5A and 5B, with exceptions to be described. In this case, the upper body thermal blanket 51 is longitudinally disposed on the inside surface 43, in alignment with the longitudinal axis 49 of the garment 42. Preferably, the upper body thermal blanket 51 is substantially centered in the inside of the garment 42. The thermal blanket may be a separate piece which is attached to the garment, or it may be formed integrally with the garment as described above in connection with FIGS. 3A and 3B. An opening 54 in the garment 42 provides access by which an air hose can connect to an inlet port of the upper body thermal blanket 51. Warmed, pressurized air flowing into the upper body thermal blanket 51 exits through apertures in the surface 55.

In FIGS. 7A through 7C, a mechanism to releasably retain the upper body thermal blanket 51 as a separate element may include a plurality of islands of pressure sensitive adhesive material, hook and eye material, snaps, or other equivalent elements as described above in connection with FIGS. 3A and 3B. A mechanism to releasably retain the upper body thermal blanket 51 as an element formed integrally with the garment includes the alternatives along the trace 60 described above in connection with FIGS. 3A and 3B. In this case, the thermal blanket may be reattached to the garment by taping.

As shown in FIGS. 7A and 7B, a second thermal blanket 90 may be releasably attached to the inside surface 43 of the garment between the upper body thermal blanket 51 and the lower hem 47. The second thermal blanket 90 is disposed transversely to the longitudinal axis 49 of the garment 42 and has an indentation 92 to accommodate the lower end of the upper body thermal blanket 51. Preferably, the second thermal blanket is formed integrally with the garment 42. A second opening 96 in the garment 42 provides access by which an air hose can connect to an inlet port of the second thermal blanket 90. Warmed, pressurized air flowing into the second thermal blanket 90 exits through apertures in the surface 97.

When worn as shown in FIG. 1, the warming device 40 of FIGS. 7A through 7C retains the warmed air within the clinical garment for comfort warming preoperatively. In this case, the warmed air is provided through the second thermal blanket 90. When the patient transitions to surgery, the second thermal blanket 90 is detached from the clinical garment 42 and then the upper body thermal blanket 51 is detached from the garment 42 and deployed as shown in FIG. 2C for therapeutic warming. Postoperatively, the thermal blanket 51 may be used alone for therapeutic heating; alternatively, the upper body thermal blanket 51 or the second thermal blanket 90 may be reattached to the clinical garment 42 for therapeutic or comfort heating.

Figures 8A, 8B:
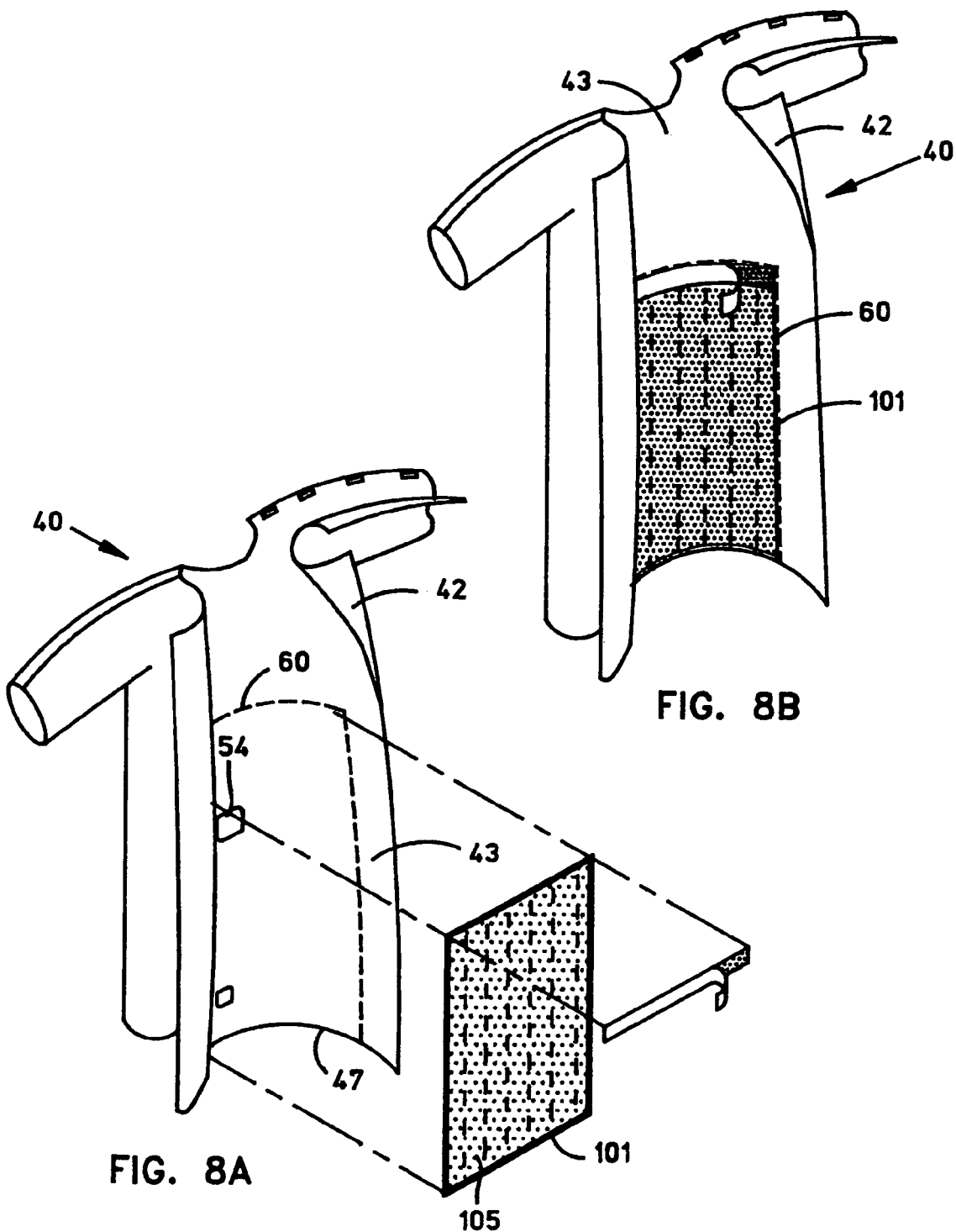
FIGS. 8A and 8B are perspective drawings showing assembly of a warming device constituted of a clinical garment and a thermal blanket disposed on the inside of the garment.

FIGS. 8A and 8B illustrate another aspect of the warming device 40 for perioperative use, constituted as described above in connection with FIGS. 3A and 3B, with exceptions to be described. In this case, a lower body thermal blanket 101 is supported centered on the inside surface 43, aligned with the lower hem 47, and may be releasably attached to the inside surface 43. The thermal blanket 101 may be a separate piece which is attached to the garment, or it may be formed integrally with the garment as described above in connection with FIGS. 3A and 3B. An opening 54 in the garment 42 provides access by which an air hose can connect to an inlet port of the lower body thermal blanket 101. Warmed, pressurized air flowing into the lower body thermal blanket 101 exits through apertures in the surface 105. A mechanism to releasably retain the lower body thermal blanket 101 as a separate element may include a plurality of islands of pressure sensitive adhesive material, hook and eye material, snaps, or other equivalent elements as described above in connection with FIGS. 3A and 3B. A mechanism to releasably retain the lower body thermal blanket 101 as an element formed integrally with the garment includes the alternatives along the trace 60 described above in connection with FIGS. 3A and 3B. In this case, the lower body thermal blanket 101 may be reattached to the garment by taping. When worn as shown in FIG. 1, the warming device 40 retains the warmed air within the clinical garment for comfort warming preoperatively. When the patient transitions to surgery, the lower body thermal blanket 101 is detached from the garment 42 and deployed as shown in FIG. 2B for therapeutic warming.

The invention claimed is:

1. A warming device for perioperative use, comprising:
   a clinical garment;
   a convective upper body thermal blanket attached to the inside of the clinical garment;
   the upper body thermal blanket including a surface and apertures in the surface through which air flows in response to inflation of the upper body thermal blanket;
   the upper body thermal blanket having a shape to extend transversely across the upper body of a person to cover the person's chest and extended arms; and,
   a mechanism acting between the clinical garment and the upper body thermal blanket and adapted to release the upper body thermal blanket from the inside of the clinical garment.

2. The warming device of claim 1, wherein the upper body thermal blanket is disposed transversely across the inside of the clinical garment.

3. The warming device of claim 1, wherein the mechanism includes lines of weakness in the clinical garment near the perimeter of the upper body thermal blanket.

4. The warming device of claim 1, wherein the mechanism is one of hook and eye material, adhesive, or snaps.

5. The warming device of claim 1, the clinical garment including opposed vertical hems, the warming device further including:
   opposed flaps formed in the opposed vertical hems;
   the upper body thermal blanket extending from one flap to the other flap;
   the flaps adapted to be folded into the inside of the clinical garment over the upper body thermal blanket; and
   means for releasably retaining the opposed flaps against the inside of the clinical garment.

6. The warming device of claim 5, wherein the means include one of hook and eye material, adhesive, or snaps.

7. The warming device of claim 1, wherein the upper body thermal blanket is disposed longitudinally along the inside of the clinical garment.

8. The warming device of claim 7, wherein the upper body thermal blanket is disposed longitudinally along the middle of the inside of the clinical garment.

9. The warming device of claim 7, wherein the mechanism includes lines of weakness in the clinical garment near the perimeter of the upper body thermal blanket.

10. The warming device of claim 7, wherein the mechanism is one of hook and eye material, adhesive, or snaps.

11. The warming device of claim 7, the clinical garment including a lower hem, the warming device further including:
    the lower hem adapted to be folded into the inside of the clinical garment over the upper body thermal blanket; and
    means for releasably retaining the lower hem against the inside of the clinical garment.

12. The warming device of claim 11, wherein the means include one of hook and eye material, adhesive, or snaps.

13. The warming device of claim 11, further including:
    a second thermal blanket attached to the clinical garment and disposed transversely across the middle of the clinical garment on a folded portion inside the clinical garment extending from the lower hem; and
    means for releasably retaining the second thermal blanket on the folded portion.

14. The warming device of claim 13, wherein the means include one of hook and eye material, adhesive, or snaps.

15. The warming device of claim 1, the clinical garment including a lower hem, the warming device further including:
    a second thermal blanket attached to the inside of the clinical garment and disposed transversely across the middle of the clinical garment between the lower hem and the upper body thermal blanket; and
    means for releasably retaining the second thermal blanket on the inside of the clinical garment.

16. The warming device of claim 15, wherein the means include one of hook and eye material, adhesive, or snaps.

17. The warming device of claim 15, wherein the second thermal blanket is shaped to receive a portion of the upper body thermal blanket.

18. The warming device of claim 15, wherein the mechanism includes lines of weakness in the clinical garment near the perimeter of the thermal blanket.

19. The warming device of claim 15, wherein the mechanism is one of hook and eye material, adhesive, or snaps.

20. The warming device of claim 15, wherein the upper body thermal blanket is disposed longitudinally along the inside of the clinical garment.

21. The warming device of claim 20, wherein the upper body thermal blanket is disposed longitudinally along the middle of the inside of the clinical garment.

22. The warming device of claim 20, wherein the mechanism includes lines of weakness in the clinical garment near the perimeter of the thermal blanket.

23. The warming device of claim 20, wherein the mechanism is one of hook and eye material, adhesive, or snaps.

24. A perioperative warming device, comprising:
a clinical garment;
a convective upper body thermal blanket attached to the inside of the clinical garment, longitudinally to the inside of the clinical garment;
the convective upper body thermal blanket including a surface and apertures in the surface through which air flows in response to inflation of the convective upper body thermal blanket;
the convective upper body thermal blanket having a shape to extend transversely across the upper body of a person to cover the person's chest and extended arms; and
means acting between the clinical garment and the convective upper body thermal blanket for detaching the convective upper body thermal blanket from the clinical garment.

25. The warming device of claim 24, wherein the means include lines of weakness in the clinical garment near the perimeter of the convective upper body thermal blanket.

26. The warming device of claim 24, wherein the means is one of hook and eye material, adhesive, or snaps.

27. A warming device, comprising:
clinical garment;
a convective upper body thermal blanket attached to the inside of the clinical garment, longitudinally along the inside of the clinical garment;
the convective upper body thermal blanket having a shape to extend transversely across the chest and arms of a person to cover the person's chest and extended arms; and
means acting between the clinical garment and the convective upper body thermal blanket for detaching the convective upper body thermal blanket from the clinical garment.

28. The warming device of claim 27, wherein the means include lines of weakness in the clinical garment near the perimeter of the convective upper body thermal blanket.

29. The warming device of claim 27, wherein the means is one of hook and eye material, adhesive, or snaps.

30. A warming device for perioperative use, comprising:
a clinical garment with an inside surface; and
at least one convective upper body thermal blanket attached to the inside surface;
the convective upper body thermal blanket having a shape to extend transversely across the upper body of a person to cover the person's chest and extended arms; and,
the convective upper body thermal blanket including a surface and apertures in the surface through which air flows in response to inflation of the convective upper body thermal blanket.

31. The warming device of claim 30, further including means acting between the clinical garment and the at least one convective upper body thermal blanket for detaching the convective upper body thermal blanket from the clinical garment.

32. The warming device of claim 31, wherein the at least one upper body thermal blanket is disposed transversely, across the inside of the clinical garment.

33. The warming device of claim 31, wherein the at least one upper body thermal blanket is disposed transversely across a lower portion of the inside of the clinical garment.

34. The warming device of claim 31, wherein the means include lines of weakness in the clinical garment near the perimeter of the convective upper body thermal blanket.

35. The warming device of claim 31, wherein the means include one of hook and eye material, adhesive, or snaps.

36. The warming device of claim 31, wherein the convective upper body thermal blanket is disposed longitudinally along the inside of the clinical garment.

37. The warming device of claim 1, wherein the clinical garment is a hospital gown.

38. The warming device of claim 24, wherein the clinical garment is a hospital gown.

39. The warming device of claim 27, wherein the clinical garment is a hospital gown.

40. The warming device of claim 30, wherein the clinical garment is a hospital gown.

* * * * *